United States Patent [19]

Hoelderich et al.

[11] Patent Number: 4,980,511
[45] Date of Patent: Dec. 25, 1990

[54] PREPARATION OF ALDEHYDES AND/OR KETONES BU CONVERSION OF EPOXIDES

[75] Inventors: Wolfgang Hoelderich, Frankenthal; Norbert Goetz, Worms; Leopold Hupfer, Friedelsheim; Helmut Lermer, Mannheim, all of Fed. Rep. of Germany

[73] Assignee: BASF Aktiengesellschaft, Ludwigshafen, Fed. Rep. of Germany

[21] Appl. No.: 100,725

[22] Filed: Sep. 25, 1987

[30] Foreign Application Priority Data

Sep. 25, 1986 [DE] Fed. Rep. of Germany ....... 3632529

[51] Int. Cl.$^5$ .............................................. C07C 45/58
[52] U.S. Cl. ................................... 568/310; 568/341; 568/384; 568/427; 568/450; 568/443
[58] Field of Search ............... 568/310, 341, 384, 386, 568/427, 450, 443

[56] References Cited

U.S. PATENT DOCUMENTS

| 4,329,506 | 5/1982 | Velenyi et al. | 568/384 |
|---|---|---|---|
| 4,401,637 | 8/1983 | Marosi et al. | 568/427 |
| 4,495,371 | 1/1985 | Neri et al. | 568/427 |
| 4,694,107 | 9/1987 | Hoelderich et al. | 568/387 |
| 4,709,097 | 11/1987 | Hoelderich et al. | 568/443 |

FOREIGN PATENT DOCUMENTS

| 0100117 | 9/1986 | European Pat. Off. | 568/427 |
|---|---|---|---|
| 3996471 | 8/1981 | Fed. Rep. of Germany | 568/427 |
| 3031637 | 3/1978 | Japan | 568/427 |
| 60-178840 | 9/1985 | Japan | 568/427 |
| 61-112040 | 5/1986 | Japan | 568/427 |
| 61-151145 | 7/1986 | Japan | 568/427 |
| 61-176547 | 8/1986 | Japan | 568/427 |

Primary Examiner—James H. Reamer
Attorney, Agent, or Firm—Keil & Weinkauf

[57] ABSTRACT

Aldehydes and ketones are prepared from epoxides of the formula

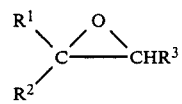

where $R^1$ and $R^2$ are each alkyl, alkenyl, aryl, alkoxy or aralkyl and $R^3$ has the same meanings or is hydrogen, by a catalytic rearrangement reaction in the presence of various catalysts, in particular zeolites of the pentasil type.

2 Claims, No Drawings

PREPARATION OF ALDEHYDES AND/OR KETONES BU CONVERSION OF EPOXIDES

The present invention relates to a process for the preparation of aldehydes and/or ketones by converting an epoxide over a zeolite, over a hydrothermally prepared phosphate, over a phosphate of B, Fe, Ce or Zr, or boric acid on a carrier, or over silica.

Processes for the preparation of aldehydes and ketones have frequently been described in the literature. For example, various processes are known in which acidic homogeneous catalysts, such as phosphoric acid, boron trifluoride diethyl etherate, tin(IV) chloride and palladium complexes, are used for the liquid-phase reaction. For the gas-phase reactions, aluminas and aluminum silicates are mentioned as catalysts for the rearrangement.

It is also known that butylene oxide can be converted to a mixture of butyraldehyde, cis/trans-but-2-enol, butanol and methyl ethyl ketone, over doped A zeolites. However, the selectivity in this reaction is unsatisfactory. Furthermore, the A zeolite catalyst cannot be regenerated after it has been deactivated by coking, since the crystal structure of the zeolite is destroyed at the temperatures of about 500° C. required for this purpose. This also applies to the preparation of 2-(4'-isobutylphenyl)propanal from 2-(4'-isobutylphenyl)-2-methyloxirane over 5 Å molecular sieves (Japanese Patent No. 3031-637).

For the conversion of propylene oxide to acetone or propionaldehyde over alkali-doped X zeolites, it is necessary to carry out the reaction in the absence of highly acidic centers.

Cyclododecanone has been obtained from epoxycyclododecane over Pd- or Rd- doped Al$_2$O$_3$; it is pointed out that zeolites are unsuitable for this reaction (Neftekhimya 16 (1976), 250–254).

European Patent No. 100,117 describes the reaction of styrene oxide and of styrene oxides which are alkyl-substituted or alkoxy-substituted in the aromatic nucleus over a titanium-containing zeolite to give β-phenylaldehydes in the liquid phase at from 30° to 100° C. The catalyst used for this purpose is prepared by an expensive procedure from very pure starting materials, such as tetraalkyl orthosilicates, tetraalkyl orthotitanates and tetrapropylammonium hydroxide. High conversions are obtained only in a reaction in a solvent, such as methanol or acetone, at from 30° to 100° C. in the liquid phase with residence times of from 1 to 1.5 hours. This means greater costs for distillation and operation. Over titanium-containing zeolites, it is only possible to convert styrene oxide and styrene oxides which are alkylated or alkoxylated in the aromatic moiety.

It is an object of the present invention to provide a process which permits the preparation of aldehydes and ketones, including those which were previously unobtainable, from the corresponding epoxides in the presence of readily available catalysts which have high activity and are easily regenerated. It is also intended to achieve high conversions and selectivities and flexible use of the catalyst with respect to the educts, in combination with long catalyst lives.

We have found that this object is achieved by a process for the preparation of aldehydes and ketones of the formula (I)

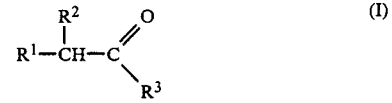

where $R^1$ and $R^2$ are each straight-chain or branched alkyl of 1 to 12 carbon atoms, straight-chain or branched alkenyl of 1 to 12 carbon atoms, cycloalkyl or cycloalkenyl, each of 5 to 8 carbon atoms, alkoxy radicals or aryl or aralkyl radicals which in turn may be substituted, and $R^3$ is hydrogen, alkyl, alkenyl, aryl or aralkyl, wherein an epoxide of the formula (II)

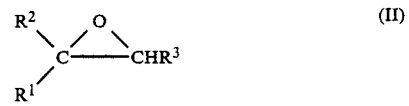

where $R^1$, $R^2$ and $R^3$ have the above meanings, is subjected to a rearrangement reaction using a readily available catalyst which has high activity and is easily regenerated.

For the purposes of the present invention, readily available catalysts which have high activity and are easily regenerated are zeolites of the pentasil type, of the mordenite type, of the erionite/chabazite type and of the L type, as well as aluminum phosphates, silicon aluminum phosphates, iron aluminum phosphates or iron silicon aluminum phosphates and boron phosphates, and phosphoric acid and/or boric acid on pumice, silica or alumina and silica.

The present invention introduces into the art a process for the preparation of aldehydes and ketones of the formula (I) from readily available starting materials of the formula (II), in which the catalysts present are readily available, have a high activity, are easily regenerated, have long lives and give high conversions and high selectivities, the said process ensuring flexible use of the catalysts with respect to the end products.

The novel process avoids the disadvantages of the known processes, these disadvantages having been mentioned at the outset. The result is surprising since previously only weakly acidic X zeolites were considered suitable and zeolites were generally considered unsuitable for rearrangement reactions. It could therefore not be expected that such excellent results would be obtained, within such wide limits and with such a great variety of educts, precisely with zeolites which are distinguished by high acidity and stringent structural parameters.

Further advantages of the novel process are the following: complete conversion and a selectivity >90% mean that there are no separation problems. Furthermore, long lives and very good yields are obtained. Other advantages are the fact that the end products can be isolated in a simple manner and as a rule reused without additional purification, and the catalysts are easy to regenerate in the event of coking. Another advantage is that the reaction can be carried out in the gas phase.

For the novel process, for example, the following epoxides can be used as starting materials: α-phenylstyrene oxide (1,1-diphenylethylene oxide), α-methylstyrene oxide, α-ethylstyrene oxide, α-isopropylstyrene oxide, 2-methyl-2,3-epoxybutane and diisobutene oxide and others.

Acidic zeolite catalysts are used as catalysts for the novel conversion of the epoxides. Zeolites are crystalline aluminosilicates which have a highly ordered structure with a rigid three-dimensional network of $SiO_4$ and $AlO_4$ tetrahedra which are linked by common oxygen atoms. The ratio of Si and Al atoms to oxygen is 1:2. The electrovalency of the aluminum-containing tetrahedra is compensated by the inclusion of cations in the crystal, for example an alkali metal or hydrogen ion. Cation exchange is possible. The voids between the tetrahedra are occupied by water molecules prior to dehydration by drying or calcination.

In the zeolites, it is also possible for other trivalent and divalent elements, such as B, Ga, Fe, Cr, Be, As or Sb, to be incorporated in the framework in place of aluminum, or the silicon can be replaced by a tetravalent element such as Ge, Ti, Zr or Hf.

Suitable catalysts are zeolites from the mordenite group or faujasite group, such as L zeolites, or finepored zeolites of the erionite or chabasite type. Particularly advantageous for the novel process are zeolites of the pentasil type. These zeolites can have different chemical compositions. The zeolites in question are aluminosilicate, borosilicate, iron silicate, gallium silicate, chromium silicate, beryllium silicate, arsenic silicate, antimony silicate and bismuth silicate zeolites or mixtures of these, and aluminogermanate, borogermanate, gallium germanate and iron germanate zeolites or mixtures of these.

The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$ and a silicon component, preferably finely divided silica, in aqueous amine solution, in particular in 1,6-hexanediamine or 1,3-propanediamine or triethylenetetramine solution, with or, in particular, without the addition of an alkali or alkaline earth, at from 100° to 220° C. under autogenous pressure. The isotactic zeolites according to German Laid-Open Application DOS 3,006,471 are also suitable. The aluminosilicate silicate zeolites obtained have an $SiO_2/Al_2O_3$ ratio of from 10 to 40,000, depending on the amounts of starting materials chosen, and can also be synthesized in an ether medium, for example in diethylene glycol dimethyl ether, in an alcoholic medium, such as methanol or butane-1,4-diol or in water.

The borosilicate zeolites, including the isotactic borosilicate zeolites, can be synthesized, for example, at from 90° to 200° C. under autogenous pressure by reacting a boron compound, e.g. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. The borosilicate zeolites, instead of being prepared in aqueous amine solution, can also be prepared in ether solution, for example in diethylene glycol dimethyl ether, or in alcoholic solution, for example in hexane-1,6-diol.

Iron silicate zeolites are obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth, at from 100° to 220° C. under autogenous pressure.

After they have been isolated, dried at from 100 to 160° C., preferably 110° C., and calcined at from 450 to 550° C., preferably from 500° to 540° C., the aluminosilicate, borosilicate and iron silicate zeolites thus prepared can be molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 95:5, preferably 75:25, silica, preferably finely divided $SiO_2$, mixtures of finely divided $SiO_2$ and finely divided $Al_2O_3$, and clay. After the molding procedure, the extrudates or pellets are dried at 110° C. for 16 hours and calcined at 500° C. for 16 hours.

The aluminosilicate and borosilicate zeolites isolated can also be molded directly after the drying procedure and subjected to calcination only after the molding procedure. The aluminosilicate and borosilicate zeolites can be used in pure form, without binder, as extrudates or pellets, examples of extrusion or peptizing assistants used being ethylcellulose, stearic acid, potato starch, formic acid, oxalic acid, acetic acid, nitric acid, ammonia, amines, silicoesters and graphite, and mixtures of these.

If, because of its method of preparation, the zeolite is present not in the catalytically active, acidic H form but, for example, in the Na form, the latter can be converted completely or partially to the desired H form by ion exchange, for example with ammonium ions, followed by calcination or by treatment with an acid.

If, when the zeolite catalysts are used according to the invention, deactivation due to coking occurs, it is advisable to regenerate the zeolites by burning off the coke deposit with air or with an air/$N_2$ mixture at from 400° to 550° C., preferably from 500° to 540° C. As a result, the zeolites regain their initial activity. The activity of the catalyst can be adjusted to give optimum selectivity with respect to the desired reaction product by precoking.

In order to obtain very high selectivity, high conversion and long catalyst lives, it is sometimes advantageous to modify the zeolites. In a suitable method of modifying the catalysts, for example, the unmolded or molded zeolites are doped with metal salts by ion exchange or by impregnation.

Advantageously, the doping is carried out as follows: the molded zeolites are initially taken in a riser tube, and an aqueous or ammoniacal solution of a halide or nitrate of the metals is passed over at from 20° to 100° C. Ion exchange of this type can be carried out with the hydrogen, ammonium and alkali metal form of the zeolite. In another possible method for applying the metals to the zeolites, the zeolite material is impregnated, for example with a halide, a nitrate or an oxide of the metals in aqueous, alcoholic or ammoniacal solution. Both ion exchange and impregnation are followed at least by drying, and if desired by repeated calcination.

In a possible embodiment, $Cs_2CO_3$ is dissolved in water and this solution is used to impregnate the molded or unmolded zeolite for a certain time, about 30 minutes. Any supernatant solution is freed from water in a rotary evaporator. Thereafter, the impregnated zeolite is dried at about 150° C. and calcined at about 550° C. This impregnation process can be carried out several times in succession in order to obtain the desired metal content. It is also possible to prepare an ammoniacal $Pd(NO_3)_2$ solution and to suspend the pure zeolite powder therein at from 40° to 100° C. for about 24 hours, while stirring. After being filtered off, dried at about 150° C. and calcined at about 500° C., the zeolite material obtained in this manner can be further processed with or without a binder to give extrudates, pellets or fluidizable material. The zeolite present in the H form is subjected to ion exchange as follows: the zeolite, in the form of extrudates or pellets, is initially taken in a column, and, for example, an ammoniacal $Pd(NO_3)_2$ solution is circulated over the said zeolite at slightly elevated temperatures of from 30° to 80° C. for from 15 to 20 hours. Thereafter, the product is washed thoroughly with water, dried at about 150° C. and calcined at about 550° C. In the case of some metal-doped zeolites, after-treatment with hydrogen is advantageous.

In another possible method of modification, the molded or unmolded zeolite material is subjected to a treatment with an acid, such as hydrochloric acid, hydrofluoric acid or phosphoric acid, and/or steam.

The silicon-rich zeolites ($SiO_2/Al_2O_3 > 10$) which can be used include the known ZSM types and ferrierite and Nu-1, as well as Silicate®, a molecular sieve, ie. a silica polymorph.

Other catalysts for the preparation of aldehydes and ketones of the formula (I) from corresponding epoxides of the formula (II) are described below. Aluminum phosphate catalysts used for the novel process are aluminum phosphates synthesized under hydrothermal conditions. The aluminum phosphates prepared under hydrothermal conditions are, for example, APO-5, APO-9, APO-11, APO-12, APO-14, APO-21, APO-25, APO-31 and APO-33. Syntheses of these compounds are described in European Patent No. 132,708 and U.S. Pat. Nos. 4,310,440 and 4,473,663.

For example, $AlPO_4$-5 (APO-5) can be synthesized by homogeneously mixing orthophosphoric acid with pseudoboehmite (Catapal SB® in water, adding tetrapropylammonium hydroxide to this mixture and then carrying out the reaction at about 150° C. for from 20 to 60 hours under autogenous pressure in an autoclave. The $AlPO_4$-5 filtered off is dried at from 100° to 160° C. and calcined at from 450 to 550° C. $AlPO_4$-9) (APO-9) can be synthesized from orthophosphoric acid and pseudoboehmite in aqueous DABCO solution (1,4-diazabicyclo[2.2.2]octane) at about 200° C. under autogeneous pressure for from 200 to 400 h. $AlPO_4$-21 (APO-21) is synthesized from orthophosphoric acid and pseudoboehmite in aqueous pyrrolidone solution at from 150° to 200° C. under autogenous pressure for from 50 to 200 hours.

The silicon aluminum phosphates used for the novel process are, for example, SAPO-5, SAPO-11, SAPO-31 and SAPO-34. The synthesis of this compound is described in European Patent No. 103,117 and U.S. Pat. No. 4,440,871. These substances are obtained by crystallization from an aqueous mixture at from 100° to 250° C. under autogenous pressure in the course of 2 hours to 2 weeks, the reaction mixture of a silicon component, an aluminum component and a phosphorus component being reacted in an aqueous solution of an organic amine. For example, SAPO-5 is obtained by mixing $SiO_2$, suspended in aqueous tetrapropylammonium hydroxide solution, with an aqueous suspension of pseudoboehmite and orthophosphoric acid and then carrying out the reaction at from 150° to 200° C. in the course of from 20 to 200 hours under autogenous pressure in a stirred autoclave. The powder which has been filtered off is dried at from 110° to 160° C. and calcined at from 450° to 550° C. Other examples of suitable silicon aluminum phosphates are ZYT-5, ZYT-6, ZYT-7, ZYT-9, ZYT-11 and ZYT-12 (Japanese Patent No. 9217-619).

Boron phosphates for the novel process can be prepared by mixing and kneading concentrated boric acid and phosphoric acid, followed by drying and calcination in an inert gas, air or steam atmosphere at from 250° to 650° C., preferably from 300° to 500° C. $CePO_4$ is also suitable for the novel process. $CePO_4$ is obtained from 52 g of $Ce(NO_3)_3 \cdot 6H_2O$ and 56 g of $NaH_2PO_4 \cdot 2H_2O$, for example by precipitation. After the filtration, the material is converted to extrudates, dried at 120° C. and calcined at 450° C. $CePO_4$ contains 47.1% by weight of Ce and 12.7% by weight of P. Other examples of suitable phosphates are $FePO_4$ and $Zr_3(PO_4)_4$.

For catalyzing the novel reaction, it is also possible to use boric acid on $SiO_2$, $Al_2O_3$ or pumice carriers, applied, for example, by impregnation or spraying. Silica too, can be used as a catalyst.

The catalysts can be used alternatively in the form of 2-4 mm extrudates, pellets having a diameter of 3-5 mm, powders having particle sizes of from 0.1 to 0.5 mm or a fluidized catalyst.

The novel conversion of the epoxides is preferably carried out in the gas phase and as a rule at from 50 to 500° C., preferably from 150° to 400° C., at a WHSV of from 0.1 to 20 $h^{-1}$, preferably from 0.5 to 5 $h^{-1}$ (g of epoxide per g of catalyst per hour), by the fixed-bed or fluidized bed method. In general, the conversion increases sharply with increasing temperature, while the selectivity decreases only slightly in a certain temperature range.

It is also possible to carry out the reaction in the liquid phase (suspension, trickle-bed or liquid-phase procedure).

The process is carried out in general under atmospheric, reduced or superatmospheric pressure, batchwise or, preferably, continuously.

Sparingly volatile or solid starting materials are used in dissolved form, for example in solution in tetrahydrofuran, toluene or petroleum ether. Dilution with inert gases, such as $N_2$, Ar or steam, is also possible.

After the reaction, the resulting aldehydes and ketones can be isolated from the reaction mixture by a conventional technique, for example by distillation; unconverted starting materials are, if necessary, recycled to the reaction. Direct further processing of the reaction products is also possible, owing to the very high yields. The process according to the invention preferentially gives the monomeric compounds. Where oligomers, for example trimeric aldehydes, are also formed, they can be separated off and cleaved by known methods to give the desired monomers.

In the conversion of the epoxides of the formula (II), the ratio of aldehyde to ketone can be influenced by the choice of the catalyst and the reaction conditions, in particular the temperature. Some aldehydes undergo rearrangement to give ketones, as described in German Laid-Open Appication DOS No. 3,419,378, or undergo dehydration to give dienes, as in German Laid-Open Application DOS No. 3,419,379.

The compounds obtainable by the novel process, some of which are novel, are important intermediates and can be further processed in a simple manner, by familiar methods, to give amines, alcohols and acids, for example by oxidation by oxygen or by reduction, eg. catalytic hydrogenation or hydrogenation under aminating conditions.

EXAMPLES 1 to 28

The reactions are carried out under isothermal conditions in a tube reactor (0.6 cm coil, 90 cm long) in the gas phase in the course of not less than 6 hours. Separation and characterization of the reaction products are effected by conventional methods. Quantitative determination of the reaction products and the starting materials is carried out by gas chromatography and by means of the CO number.

The catalysts used in the Examples are:

Catalyst A

An aluminosilicate zeolite of the pentasil type is prepared under hydrothermal conditions, under autogenous pressure and at 150° C., from 650 g of finely divided $SiO_2$ and 203 g of $Al_2(SO_4)_3 \cdot 18H_2O$ in 10 kg of aqueous 1,6-hexanediamine solution (mixture, 50:50% by weight) in a stirred autoclave. The crystalline reaction product is filtered off and washed thoroughly, after which it is dried at 110° C. for 24 hours and calcined at 500° C. for 24 hours. The aluminosilicate zeolite contains 92.8% by weight of $SiO_2$ and 4.2% by weight of $Al_2O_3$.

Catalyst A is obtained by molding the pure aluminosilicate zeolite with a molding assistant to give 2 mm extrudates, drying the extrudates at 110° C. for 16 hours and calcining them at 500° C. for 24 hours.

Catalyst B

A borosilicate zeolite of the pentasil type is prepared, in a hydrothermal synthesis, from 640 g of finely divided $SiO_2$, 122 g of $H_3BO_3$ and 8 kg of an aqueous 1,6-hexanediamine solution (mixture, 50:50% by weight) at 170° C. under autogenous pressure in a stirred autoclave. The crystalline reaction product is filtered off and washed thoroughly, after which it is dried at 100° C. for 24 hours and calcined at 500° C. for 24 hours. This borosilicate zeolite is composed of 94.2% by weight of $SiO_2$ and 2.3% by weight of $B_2O_3$.

This material is molded with a molding assistant to give 2 mm extrudates, which are dried at 110° C. for 16 hours and calcined at 500° C. for 24 hours.

Catalyst C

Catalyst C is prepared from a commercial mordenite (Zeolon 900 H®), ion exchange with 20% strength ammonium chloride solution being carried out in order to reduce the residual sodium content to 0.025% by weight (Na value after drying at 110° C. and calcination at 500° C.).

Catalyst D

In the preparation of catalyst D a commercial mixture of erionite/chabazite (Zeolon 500®) is subjected to ion exchange with 20% strength aqueous ammonium chloride solution until the material calcined at 500° C. has a residual sodium content of 0.11% by weight or less.

Catalyst E

A commercial L-zeolite (Baylith L®) is molded with boehmite in a weight ratio of 80:20 to give 2 mm extrudates. Drying at 110° C. for 16 hours and calcination at 500° C. for 16 hours give the ready-prepared catalyst E.

Catalyst F

The iron silicate zeolite of the pentasil type is synthesized under hydrothermal conditions, under autogenous pressure and at 165° C., from 273 g of waterglass, dissolved in 253 g of an aqueous 1,6-hexanediamine solution (mixture, 50:50% by weight), and 31 g of iron sulfate, dissolved in 21 g of 96% strength sulfuric acid and 425 g of water in a stirred autoclave in the course of 4 days. The zeolite is filtered off, washed thoroughly, dried at 110° C. for 24 hours and calcined at 500° C. for 24 hours. The resulting iron silicate zeolite has an $SiO_2/Fe_2O_3$ ratio of 17.7 and an $Na_2O$ content of 1.2% by weight. The catalyst is converted to 2.5 mm extrudates, which are dried at 110° C. for 16 hours and calcined at 500° C. for 24 hours. These extrudates are treated with 20% strength aqueous $NH_4$ solution by a conventional method until the Na content is 0.1% by weight (after calcination at 500° C. for 5 hours).

Catalyst G $AlPO_4$-12 (APO-12) is synthesized in the same way as APO-9 (catalyst L), 60 g of ethylenediamine being used instead of 112 g of DABCO. The reaction is carried out at 200° C. for 24 hours. The material synthesized in this manner, dried at 120° C. and calcined at 500° C. for 16 hours contains 55.5% by weight of $P_2O_5$ and 39.7% by weight of $Al_2O_3$. APO-12 is molded in the same way as APO-9.

Catalyst H $AlPO_4$-21 (APO-21) is synthesized by stirring together 200 g of 98% strength phosphoric acid, 156 g of precipitated aluminum hydroxide and 71 g of pyrrolidone in 900 g of water and then carrying out the reaction at 200° C. under autogenous pressure in the course of 91 hours. The product dried at 120° C. and calcined at 500° C. contains 56.5% by weight of $P_2O_5$ and 43.4% by weight of $Al_2O_3$. This $AlPO_4$-21 is converted with an extrusion assistant to 2 mm extrudates, which are dried at 110° C. and calcined at 500° C. for 16 hours.

Catalyst I

Silicon aluminum phosphate-5 (SAPO-5) is prepared from a mixture of 200 g of 98% strength phosphoric acid, 136 g of boehmite, 60 g of 30% strength silica sol, 287 g of tripropylamine and 587 g of $H_2O$. This mixture is reacted at 150° C. for 168 hours under autogenous pressure. After filtration, the crystalline product is dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is converted with an extrusion assistant to 3 mm extrudates, which are dried at 120° C. and calcined at 500° C.

Catalyst J

Silicon aluminum phosphate-11 (SAPO-11) is synthesized from a mixture of 200 g of $H_3PO_4$, 136 g of boehmite, 60 g of 30% strength silica sol, 91 g of dipropylamine and 890 g of water. The reaction is carried out at 200° C. for 96 hours under autogenous pressure. After filtration, the product is dried at 120° C. and calcined at 500° C. SAPO-11 contains 47.7% by weight of $P_2O_5$, 39.4% by weight of $Al_2O_3$ and 6.4% by weight of $SiO_2$. This crystalline product is converted with an extrusion assistant to 3 mm extrudates, which are dried at 120° C. and calcined at 500° C. for 16 hours.

Catalyst K $BPO_4$ is prepared by combining 49 g of $H_3BO_3$ with 117 g of 75% strength $H_3PO_4$ in a kneader, evaporating off the excess water and converting the reaction product to 3 mm extrudates. These extrudates are dried at 100° C. and calcined at 350° C. Catalyst K contains 8.77% by weight of B and 28.3% by weight of P.

Catalyst L

AlPO$_4$-9 (APO-9) is synthesized by dissolving 200 g of 98% strength phosphoric acid, and suspending 136 g of boehmite, in 400 g of water, adding an aqueous solution of 112 g of diazabicyclo[2.2.2]octane (DABCO) and 320 g of H$_2$O, and reacting this mixture in a stirred autoclave at 200° C. in the course of 336 hours under autogenous pressure. The crystalline material is filtered off and then dried at 120° C. and calcined at 500° C. for 16 hours. The AlPO$_4$-9 synthesized in this manner contains 49.0% by weight of P$_2$O$_5$ and 37 1% by weight of Al$_2$O$_3$. This material is converted with an extrusion assistant to 3 mm extrudates, which are dried repeatedly at 120° C. and calcined at 500° C. for 6 hours.

Catalyst M

SiO$_2$, commercially available as D11-11®.

Catalyst N

KC-Trockenperlen WS® containing about 97% of SiO$_2$ and about 3% of Al$_2$O$_3$ are impregnated with H$_3$BO$_3$ dissolved in CH$_3$OH, and dried at 110° C. and calcined at 500° C. for 5 hours. The boron content is 15.7% by weight (B$_2$O$_3$).

The experimental results are summarized in the tables below.

TABLE 1

| Example | 1 | 2 | 3 | 4 | 5 | 6 |
|---|---|---|---|---|---|---|
| Starting material | 2-Methyl-2,3-epoxybutane | | | | | |
| Catalyst | A | A | A | A | B | K |
| Temperature | 150° C. | 200° C. | 250° C. | 300° C. | 300° C. | 300° C. |
| WHSV | 1.8 h$^{-1}$ | 2.4 h$^{-1}$ | 1.8 h$^{-1}$ | 1.8 h$^{-1}$ | 1.8 h$^{-1}$ | 1.8 h$^{-1}$ |
| Conversion % | 100 | 100 | 100 | 100 | 100 | 100 |
| Desired products in the reacted mixture in % by weight | | | | | | |
| Methyl isopropyl ketone | 51.6 | 47.4 | 51.3 | 72.5 | 77.3 | 59.4 |
| Pivalaldehyde | 40.4 | 39.8 | 34.6 | 8.8 | 4.6 | 5.0 |
| Isoprene | 7.4 | 12.4 | 13.5 | 17.3 | 15.8 | 25.0 |

TABLE 2

| Example | 7 | 8 | 9 | 10 | 11 | 12 | 13 | 14 |
|---|---|---|---|---|---|---|---|---|
| Starting material | 2-Methylstyrene oxide | | | | | | | |
| Catalyst | A | B | B | K | L | G | M | J |
| Temperature | 300° C. | 250° C. | 300° C. | 300° C. | 300° C. | 300° C. | 300° C. | 300° C. |
| WHSV | 2.5 h$^{-1}$ | 1.7 h$^{-1}$ | 2.5 h$^{-1}$ | 2.3 h$^{-1}$ | 2.3 h$^{-1}$ | 2.3 h$^{-1}$ | 2.5 h$^{-1}$ | 2.5 h$^{-1}$ |
| Conversion % | 100 | 100 | 100 | 100 | 100 | 100 | 100 | 100 |
| Desired products in the reacted mixture in % by weight | | | | | | | | |
| 2-Phenylpropanal | 61.1 | 76.0 | 78.8 | 82.4 | 87.8 | 47.7 | 92.4 | 72.6 |
| Phenylacetone | 18.3 | 16.5 | 11.7 | 11.3 | 0.9 | 28.8 | 1.2 | 3.1 |

TABLE 3

| Example | 15 | 16 | 17 | 18 |
|---|---|---|---|---|
| Starting material | 1,1-Diphenylethylene oxide[1] | | | |
| Catalyst | A | A | B | K |
| Temperature | 300° C. | 350° C. | 300° C. | 300° C. |
| WHSV | 2.0 h$^{-1}$ | 2.2 h$^{-1}$ | 2.2 h$^{-1}$ | 2.1 h$^{-1}$ |
| Conversion % | 100 | 100 | 100 | 100 |
| Desired products in the reacted mixture in % by weight[2] | | | | |
| Diphenylacetaldehyde | 76.7 | 69.3 | 98.5 | 93.3 |
| Phenyl benzyl ketone | 21.5 | 26.5 | 0.7 | 1.9 |

[1]1,1-Diphenylethylene oxide dissolved in THF in a weight ratio 50:50
[2]Calculated without THF

TABLE 4

| Example | 19[2] | 20[2] | 21[2] | 22[2] | 23[2] | 24[2] | 25[2] | 26[2] | 27[2] | 28 |
|---|---|---|---|---|---|---|---|---|---|---|
| Starting material | Diisobutylene oxide[1] | | | | | | | | | |
| Catalyst | A | B | C | D | E | L | J | N | M | F |
| Temperature | 300° C. | 300° C. | 300° C. | 300° C. | 300° C. | 300° C. | 300° C. | 300° C. | 300° C. | 300° C. |
| WHSV | 2.0 h$^{-1}$ | 2.0 h$^{-1}$ | 1.8 h$^{-1}$ | 1.9 h$^{-1}$ | 2.0 h$^{-1}$ | 1.8 h$^{-1}$ | 1.6 h$^{-1}$ | 2.3 h$^{-1}$ | 2.0 h$^{-1}$ | 1.9 h$^{-1}$ |
| Conversion % | 100 | 100 | 100 | 100 | 100 | 100 | 100 | 100 | 100 | 100 |
| Desired products in the reacted mixture in % by weight | | | | | | | | | | |
| 2,2,4-Trimethyl-pentanal | 66.5 | 68.8 | 67.5 | 57.2 | 64.8 | 69.8 | 70.8 | 63.6 | 69.9 | 62.7 |

[1]The diisobutylene oxide mixture used contains 70.9% by weight of 2,2,4-trimethyl-4,5-epoxypentane and 20.9% by weight of 2,2,4-trimethyl-3,4-epoxypentane
[2]Diisobutylene oxide mixture diluted with THF in a weight ratio of 50:50

We claim:

1. A process for the preparation of aldehydes and ketones of the formula (I)

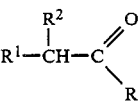

where $R^1$ and $R^2$ are each straight-chain or branched alkyl of 1 to 12 carbon atoms, cycloalkyl of 5 to 8 carbon atoms, alkoxy radicals or aryl or aralkyl radicals which in turn may be substituted, and $R^3$ is hydrogen, alkyl, aryl or aralkyl, wherein an epoxide of the formula (II)

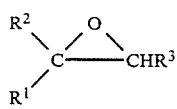 (II)

where $R^1$, $R^2$ and $R^3$ have the above meanings, is subjected to a catalytic rearrangement reaction in the gas phase at 150° to 400° C. over a zeolite selected from the group consisting of mordenite, faujasite, L-zeolites, fine-pored zeolites of the erionite and chabasite type, and aluminosilicate, borosilicate, iron silicate, gallium silicate, chromium silicate, beryllium silicate, aresenic silicate, antimony silicate, bismuth silicate, aluminogermanate, borogermanate, gallium germanate and iron germanate zeolites of the pentasil type, and a silica polymorph.

2. A process as claimed in claim 1 wherein α-methylstyrene, diisobutylene oxide, 2-methyl-2,3-epoxybutane or 1,1-diphenylethylene oxide is used as the compound of the formula II.

* * * * *

UNITED STATES PATENT AND TRADEMARK OFFICE
CERTIFICATE OF CORRECTION

PATENT NO. : 4,980,511

DATED : December 25, 1990

INVENTOR(S) : HOELDERICH et al.

It is certified that error appears in the above-identified patent and that said Letters Patent is hereby corrected as shown below:

On the title page, item [54], and in column 1, the title should read:

PREPARATION OF ALDEHYDES AND/OR KETONES
BY CONVERSION OF EPOXIDES

Signed and Sealed this

Twenty-first Day of April, 1992

Attest:

HARRY F. MANBECK, JR.

*Attesting Officer*   *Commissioner of Patents and Trademarks*